United States Patent
Henry et al.

(10) Patent No.: US 9,050,636 B2
(45) Date of Patent: Jun. 9, 2015

(54) METHOD AND DEVICE FOR CLEANING AN INTRAMEDULLARY REAMER

(71) Applicants: Catherine Campbell Henry, Great Falls, VA (US); Haider Inam, Charlottesville, VA (US); Ossman Steven Cossio, Springfield, VA (US); Edwin Lu, Blacksburg, VA (US); Claire Josephine Stump, Arlington, VA (US); Courtney Marie Lawson, Burke, VA (US); Eric Michael Moran, Charlottesville, VA (US); Narotham Badrish, Fairfax, VA (US); Daniel Robert Monaco, Herndon, VA (US)

(72) Inventors: Catherine Campbell Henry, Great Falls, VA (US); Haider Inam, Charlottesville, VA (US); Ossman Steven Cossio, Springfield, VA (US); Edwin Lu, Blacksburg, VA (US); Claire Josephine Stump, Arlington, VA (US); Courtney Marie Lawson, Burke, VA (US); Eric Michael Moran, Charlottesville, VA (US); Narotham Badrish, Fairfax, VA (US); Daniel Robert Monaco, Herndon, VA (US)

(*) Notice: Subject to any disclaimer, the term of this patent is extended or adjusted under 35 U.S.C. 154(b) by 0 days.

(21) Appl. No.: 14/499,671

(22) Filed: Sep. 29, 2014

(65) Prior Publication Data
US 2015/0013714 A1    Jan. 15, 2015

(51) Int. Cl.
| B08B 3/12  | (2006.01) |
| A61B 19/00 | (2006.01) |
| A61L 2/18  | (2006.01) |
| A61L 2/025 | (2006.01) |

(52) U.S. Cl.
CPC .............. *B08B 3/12* (2013.01); *A61B 2019/343* (2013.01); *A61B 19/34* (2013.01); *A61L 2/18* (2013.01); *A61L 2/025* (2013.01)

(58) Field of Classification Search
None
See application file for complete search history.

(56) References Cited

U.S. PATENT DOCUMENTS

| 5,628,971 A * | 5/1997 | Norman ................. 422/301 |
| 6,413,196 B1 * | 7/2002 | Crowson ................. 482/118 |
| 6,494,222 B1 * | 12/2002 | Mitsumori et al. ........ 134/184 |
| 2012/0231177 A1 * | 9/2012 | Wei et al. ................. 427/523 |
| 2013/0186429 A1 * | 7/2013 | Morita et al. ............. 134/1 |

\* cited by examiner

*Primary Examiner* — Nicole Blan
(74) *Attorney, Agent, or Firm* — Lee, Hong, Degerman, Kang & Waimey

(57) ABSTRACT

A device arranged to apply a linear tension to an intramedullary reamer for ultrasonic cleaning, and a corresponding method thereof.

1 Claim, 8 Drawing Sheets

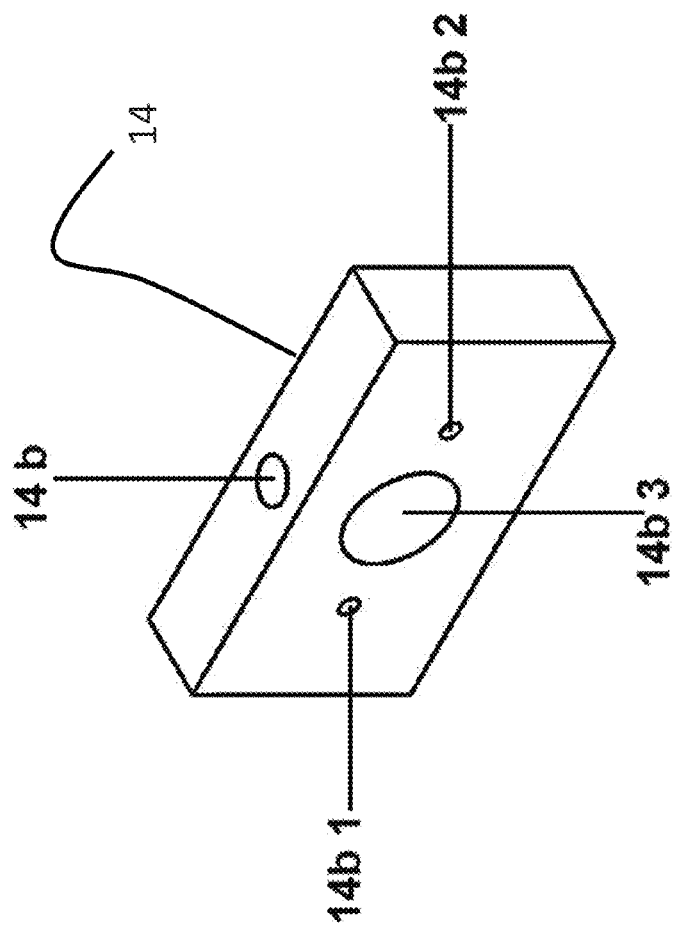

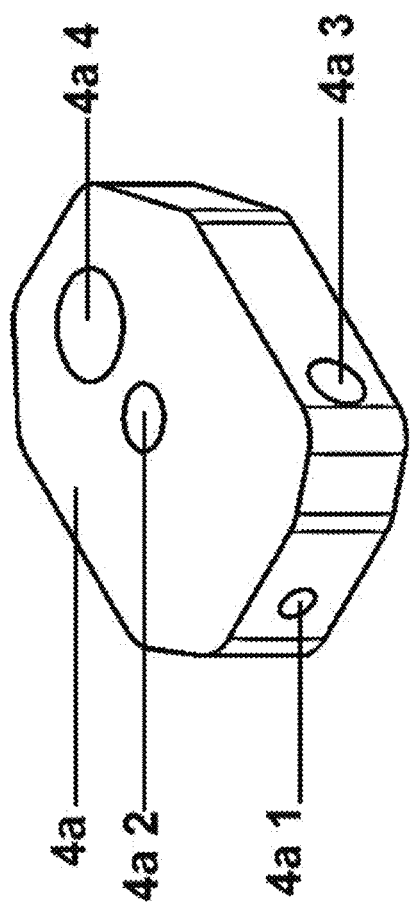

METHOD AND DEVICE FOR CLEANING AN INTRAMEDULLARY REAMER

BACKGROUND OF THE INVENTION

The medullary cavity (medulla, innermost part) is the central cavity of bone shafts where red bone marrow and/or yellow bone marrow (adipose tissue) is stored; hence, the medullary cavity is also known as the marrow cavity. Located in the main shaft (cortical bone) of a long bone (diaphysis) (consisting mostly of compact bone), the medullary cavity has walls composed of spongy bone (cancellous bone) and is lined with a thin, vascular membrane (endosteum). However, the medullary cavity is the area inside any bone (long, flat, etc.) that holds the bone marrow. This area is involved in the formation of red blood cells and white blood cells.

Intramedullary is a medical term meaning the inside of a bone. Examples include intramedullary rods used to treat bone fractures in orthopedic surgery and intramedullary tumors occurring in some forms of cancer or benign tumors such as an enchondroma.

An intramedullary reamer is a surgical instrument used in orthopedics to drill a hole into bone to allow a space for a prosthesis or appliance to sit. As shown in FIG. 1, a typical reamer includes three parts: a rasp tip or bit (A1) that is connected to a flexible body (B1) that is connected to a reamer driver via a connector (C1). FIG. 2A shows a typical reamer and manual hand driver. FIG. 2B shows a typical reamer and electromechanical driver. As seen in FIG. 3, the flexible body includes two layers of stainless steel coils that are wound in opposite directions, thereby permitting bending and twisting while reaming. However, when the flexible body bends, biodebris can collect within the corresponding gaps of the stainless steel coils. These gaps are very difficult to clean between uses.

Traditional cleaning methods include handwashing, to include bending the flexible body to expose the gaps for cleaning. The handwashing is followed by ultrasonic cleaning and sanitization. However, the traditional cleaning methods often do not permit easy and thorough access into the gaps. The traditional cleaning methods are suboptimal because when a bending force is applied to one side of the flexible body, the interior of the coils on the one side becomes more expose while the interior of the coils on the other side become more compressed and less exposed. Therefore, while some biodebris can be accessed, other biodebris becomes further compressed and lodged within the flexible body. Repeated bending and cleaning, while handwashing and/or while ultrasonic cleaning, can be burdensome and may not result in 100% exposure and cleaning. In short, the traditional cleaning methods do not permit easy and thorough removal of all bioburden. That is, even when the reamer appears clean, it is likely to have blood and bone marrow lodged into small areas between the spirals and within the cracks. If bioburden is still on the reamer, it cannot be properly sanitized. In addition, hidden bioburden poses a threat to patient health during surgery. It is necessary, therefore, to design a device that can effectively clean bioburden from the cracks and the hollow inner portion of the reamer.

Thus, as discovered by the present inventors, what is needed is an improved method and device for cleaning biodebris from the interior of the coils of the flexible body of an intramedullary reamer.

SUMMARY OF THE INVENTION

In one embodiment, there is a device arranged to apply a linear tension to an intramedullary reamer for ultrasonic cleaning The device includes: a columnar water-tight chamber; one or more ultrasonic transducers affixed to an outer surface of the columnar water-tight chamber; means for securing the intramedullary reamer within the columnar water-tight chamber; and means for applying a linear tension to the secured intramedullary reamer so as to expose an interior portion of the intramedullary reamer for ultrasonic cleaning In another embodiment, there is a method for cleaning an intramedullary reamer. The method includes: securing the intramedullary reamer within a columnar water-tight chamber, the columnar water-tight chamber having one or more ultrasonic transducers affixed to an outer surface thereof; applying a linear tension to the secured intramedullary reamer so as to expose an interior portion of the intramedullary reamer for ultrasonic cleaning; and activating the one or more ultrasonic transducers after a liquid has been added to the columnar water-tight chamber.

A DESCRIPTION OF THE DRAWINGS

FIG. 6 is an image of a second shaft collar of an intramedullary reamer according to an embodiment of the invention;

FIG. 7 is a drawing of a cable connector according to an embodiment of the invention.

DETAILED DESCRIPTION OF THE INVENTION

In the following description, various sizes, shapes and materials are disclosed when discussing various components of the present invention. These sizes, shapes and materials are non-limiting examples that may be replaced with other sizes, shapes and materials.

Figure 1:
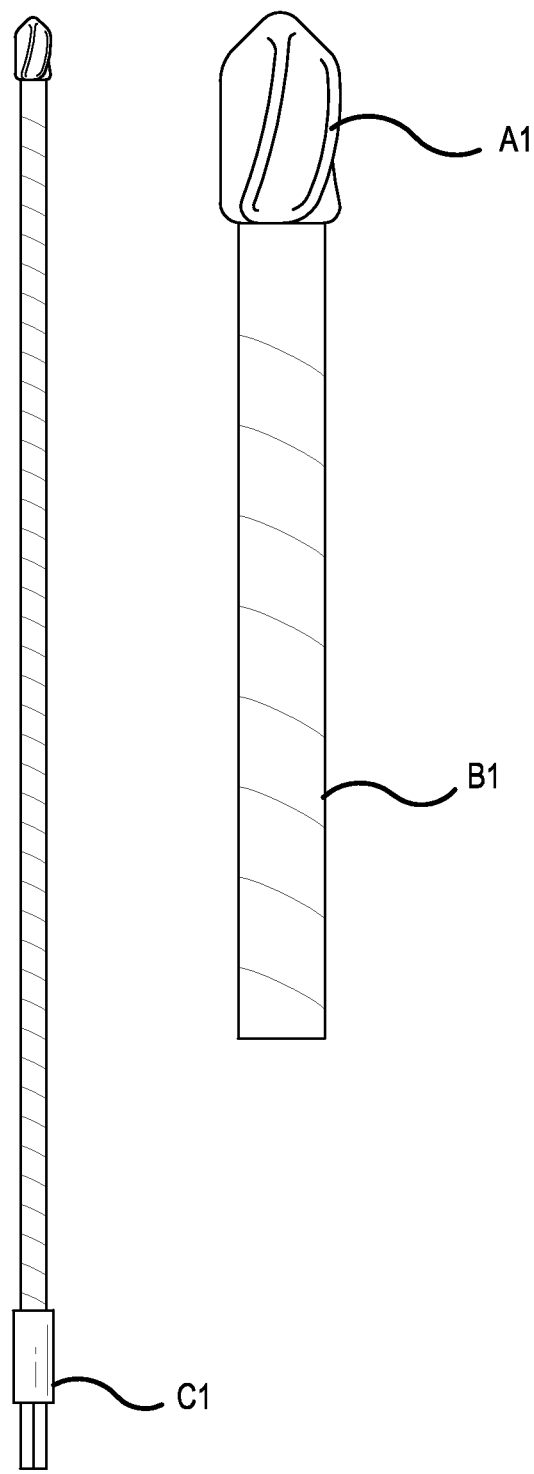
FIG. 1 is an image of a typical intramedullary reamer.
Figure 2A:
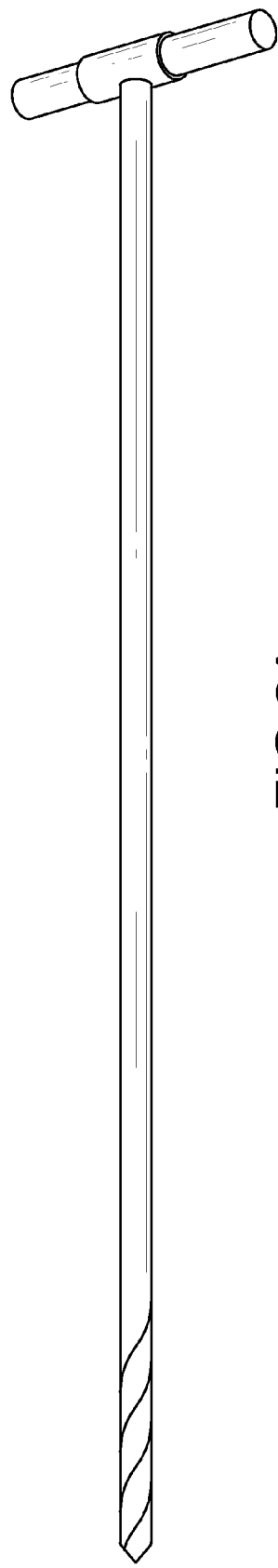
FIGS. 2A-2B are images of typical intramedullary reamer and corresponding drivers.
Figure 2B:
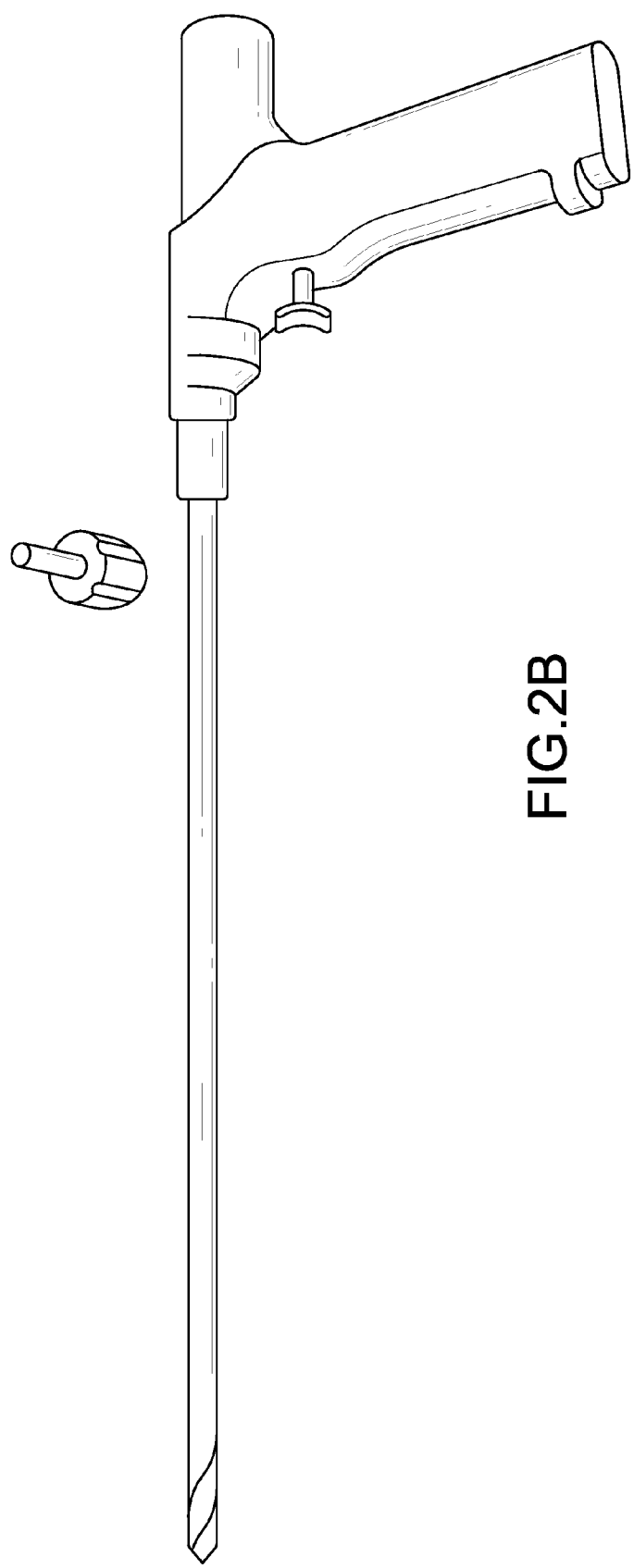
Figure 3:
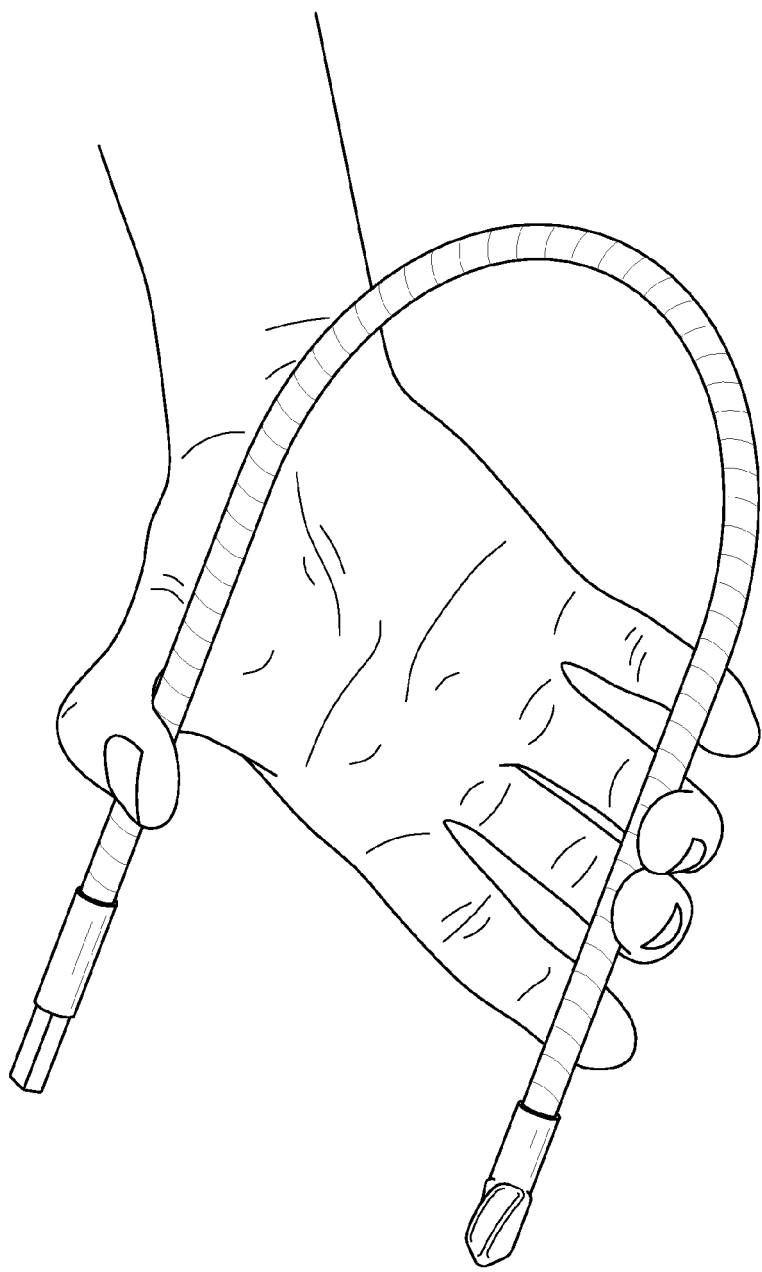
FIG. 3 is an image of a typical intramedullary reamer that has been bent.
Figure 4:
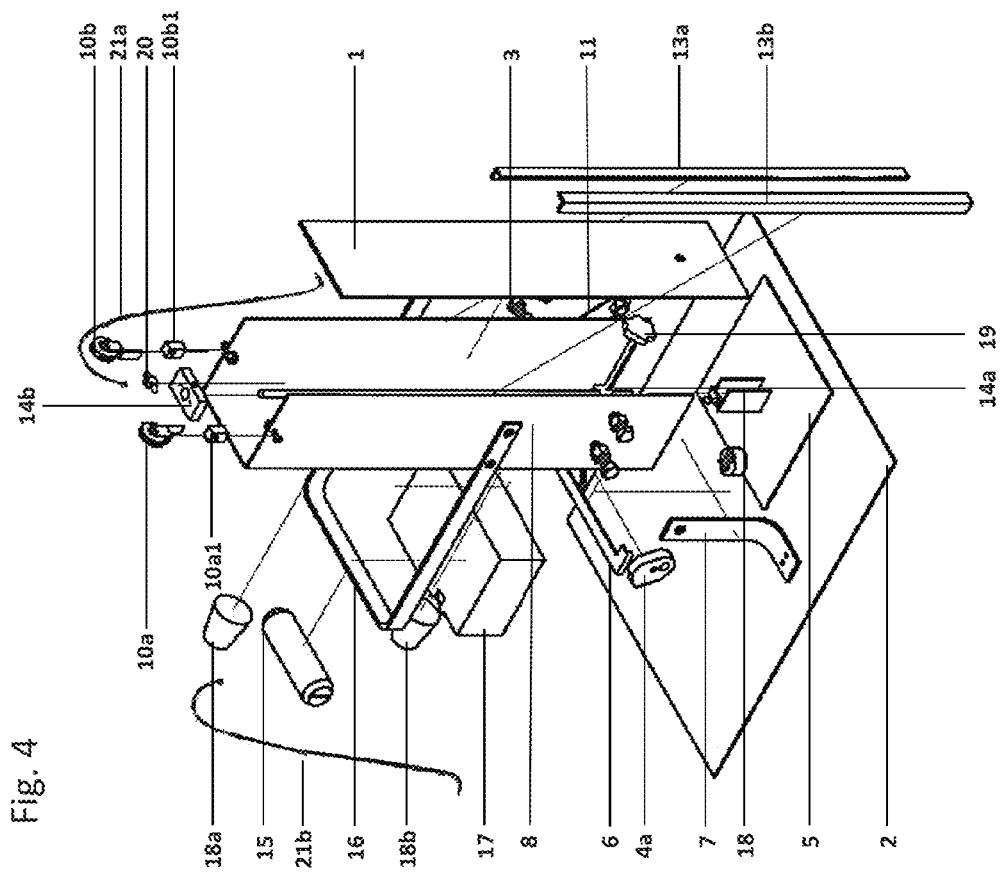
FIG. 4 is an exploded image of an intramedullary reamer according to an embodiment of the invention.
Figure 5:
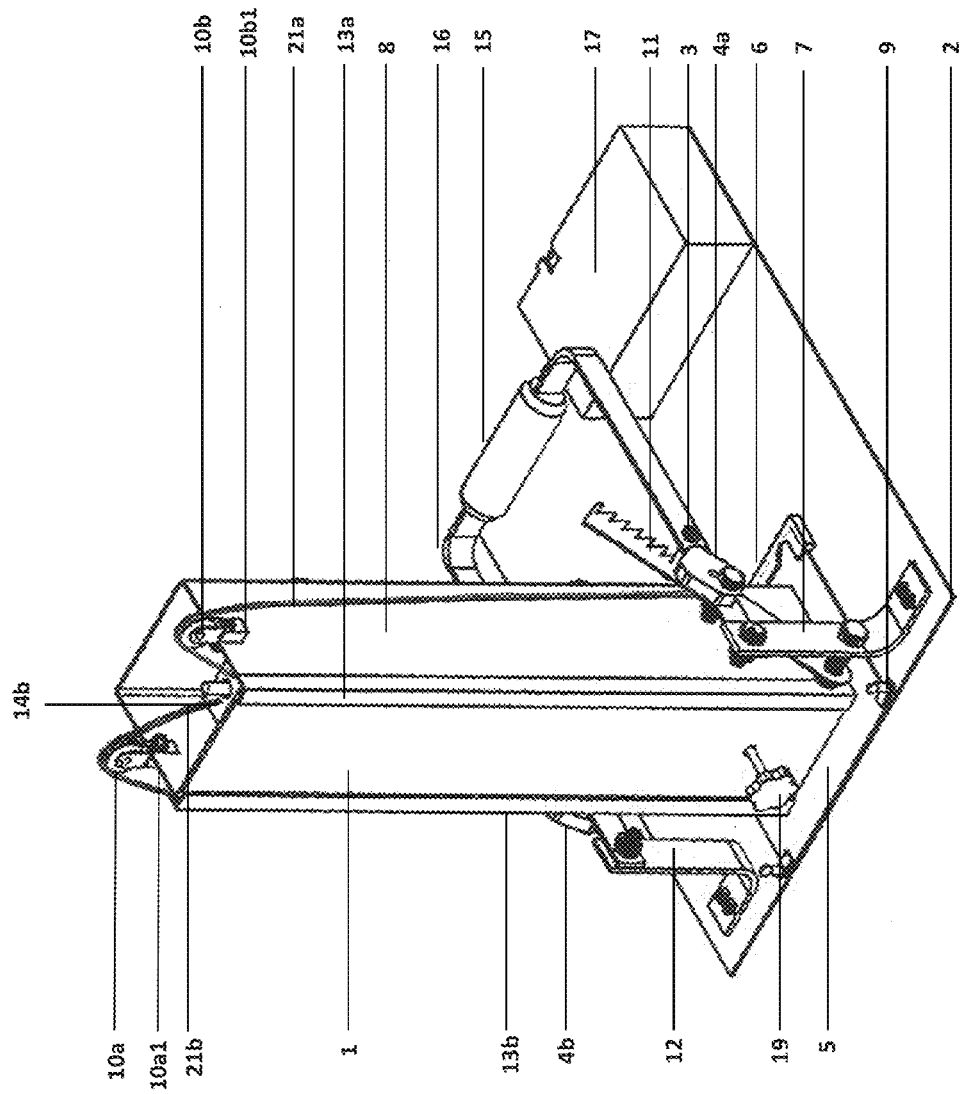
FIG. 5 is a perspective image of an intramedullary reamer according to an embodiment of the invention.

FIG. 4 is an exploded image of an intramedullary reamer according to an embodiment of the invention. FIG. 5 is a perspective image of an intramedullary reamer according to an embodiment of the invention. Major components include a columnar ultrasonic cleaning tank attached to a base (2) and a linear tension application device that is attached to the base and to the columnar ultrasonic cleaning tank.

As shown in FIGS. 4-5, the columnar ultrasonic cleaning tank is rectangular having an open top and includes one transparent face (1) (acrylic, glass, plastic or another clear material) and three non-transparent faces (8) (aluminum, carbon fiber, plastic or another material). The transparent face (1) is affixed to two of the non-transparent faces (8) by way of formed metal pieces (13a and 13b) that wrap around the corners formed between the transparent face (1) and the non-transparent faces (8), and that are glued or otherwise affixed to form a water-tight seal such that all four faces form a vertically oriented rectangle. The non-transparent faces (8) are securely attached (e.g., welded, glued or otherwise affixed) to a plate (5) to form a water-tight chamber. However, other shapes (e.g., tubular) and materials may be used. The transparent face (1) permits observation during the cleaning process. In a non-limiting embodiment, the columnar rectangular tank measures 2 inches by 2 inches in order to minimize space while still having the capacity to clean the reamer. Also, alternative chamber sizes, shapes, constructions and materials may be used to form the water-tight chamber.

In the shown embodiment, two ultrasound transducers (18a and 18b) are attached to the aluminum face that is opposite from the transparent face (1). A first transducer (18a) is placed approximately $\frac{1}{4}^{th}$ of the height of the columnar tank and a second transducer (18b) is placed approximately $\frac{3}{4}^{th}$ of the height of the columnar tank. However, the ultrasonic transducers may vary in number, size and placement around the columnar tank. The ultrasonic transducers are electrically connected to a variable speed electrical power source (17) that may be fixedly or detachably connected to a base (2). The base (2) may be any sturdy metallic or non-metallic material. The material for the base (2) should also be light enough to permit easy carrying. Handles (not shown) may be affixed to the base (2) to facilitate carrying and positioning of the device.

As noted above, the columnar tank is welded or otherwise secured to a plate (5). The plate (5) is wider than the columnar tank (e.g., 4"×4") and is arranged to slide into a groove formed between a receiving element (6) and the base (5), the receiving element (6) being affixed to the base (2) of the cleaner, the receiving element (6) having a top end wide enough to accommodate a corresponding top side of the plate (5) within the groove and having two side ends forming side grooves and that are equal to or shorter than the corresponding side ends of the plate. When the plate is slid into place within the grooves between the three sides of the receiving element and the base, the columnar tank is stably and detachably mounted onto the plate (5). To empty the columnar tank of water and biodebris, and/or to sanitize the columnar tank after use, the columnar tank may be slid out from the groove for handling. The receiving element (6) may be metal or plastic, and may be welded, glued or screwed to the base (2).

To evenly expose the interior of the coils of the reamer to the effects of ultrasonic cleaning, lateral tension is applied to the reamer by a first shaft collar (14a) and second shaft collar (14b) of the linear tension application device that are connectable to both ends of the reamer. The two shaft collars apply the lateral tension as follows.

The first shaft collar (14a) is securely fixed (e.g., welded) to a stand (18) that is welded or otherwise securely fixed to the plate (5) that forms the bottom of the interior of columnar ultrasonic tank. The stand (18) has a height arranged such that a neck of the bit (A1) of the reamer passes through the first shaft collar (14a) without the bit (A1) of the reamer touching the base (5) of the columnar tank. A first screw (19) passes from a side eye of the first shaft collar (14a) to the outside of the columnar tank via the transparent face (1) via a watertight hole. The hole is made watertight via a grommet or washer placed within the hole, with the first screw (19) passing through the grommet. The exterior end of the first screw (19) may include a first handle that enables tightening the first screw (19) to secure the neck of the bit (A1) of the reamer within the first shaft collar (14a).

The second shaft collar (14b) is configured to be placed on the connector (C1) of the reamer before the reamer is to be inserted into the columnar tank. A second screw (20) passes from a side eye of the second shaft collar (14b). The exterior end of the second screw (20) is attached to a second handle that enables tightening the second screw (20) to secure the connector (C1) of the reamer within the second shaft collar (14b).

In the preceding discussion, the bit (A1) of the reamer is placed in the first shaft collar (14a). The ensures that the end of the bit (A1) is exposed to the ultrasonic cleaning, even if the water level of the columnar tank is below the level of the second shaft collar (14b). However, it is also possible for the connector end (C1) of the reamer to be secured in the first shaft collar (14A). Also, the size of the center hole of each shaft collar is sized to accommodate various reamer diameters. These various reamer diameters are secured with the first screw (19) and second screw (20).

In one embodiment, as seen in FIG. 6, a first end of two cables (21a and 21b) pass through corresponding holes (14b1 and 14b2) on opposite sides of the center hole (14b3) of the second shaft collar (14b). The cables may be made of metal, high strength polymer or another high tensile strength material. In one embodiment, the ends of the two cables (21a and 21b) are shaped, knotted or otherwise configured to prevent the cables from slipping out of the second shaft collar (14b). In another embodiment, the ends of the two cables (21a and 21b) are detachably connected so that the cables and/or second shaft collar (14b) can be removed/replaced.

The two cables (21a and 21b) are detachably placed within a crevice of respective pulleys (10a and 10b) that are fixedly attached to the top of the columnar tank by corresponding assemblies (10a1 and 10b1). Preferably, the two pulleys (10a and 10b) are attached to the two aluminum faces (8) that connect to the transparent face (1), respectively.

A second end of the two cables (21a and 21b) are attached to opposite ends of a lever (16, hereinafter U-bar) that is located outside the container. The U-bar (16) has a handle (15) and is attached to the base (2) of the cleaner via first and second connectors (7 and 12). Here, the first and second connectors (7 and 12) are L-shaped flanges which are securely fastened to the base (2). However, methods of connection different from the L-shaped flanges may be used. The second ends of the two cables (21a and 21b) are attached to the U-bar (16) via respective machined cable holders (4a and 4b). The cable holders (4a and 4b) are connected to the U-bar (16) via a bolt and nut through a bolt hole (e.g., 4a4 in FIG. 7). A diameter of the bolt is smaller than a corresponding hole of respective cable holders so as to allow the cable holders (4a and 4b) to swivel around their respective bolts. The second ends of the two cables (21a and 21b) are threaded into an edge hole (e.g., 4a1) and out of a surface hole (e.g., 4a2) of the respective cable holders (4a and 4b). An amount of cable that passes out of the surface hole (4b2) is adjustable, with a set screw (e.g., 4a3) placed in each of the respective cable holders (4a and 4b) to secure the desired length of cable. In one embodiment, these ends of the two cables (21a and 21b) are also shaped, knotted or otherwise configured to prevent slipping out of the respective cable holders (4a and 4b).

The length of the two cables (21a and 21b) that passes through the cable holders (4a and 4b) is set via the set screws (e.g., 4a3) to accommodate various length reamers and/or to vary the amount of tension applied to a reamer that is secured by the first and second shaft collars (14a and 14b).

After the reamer is secured in the columnar tank with the shaft collars (14a and 14b), a lateral tension is applied to the reamer via the two cables (21a and 21b) by manually pressing down on the U-bar (16). By increasing the tension, the coils of the reamer are linearly stretched, thereby controllably exposing the interior of the reamer flexible body (1B) to the ultrasonic cleaning along an entire length of the reamer flexible body (1B).

A ratchet (11) attached to the base (2) is configured used to hold down the U-bar (16) by clipping onto a bolt (3) that extends inward from the U-bar (16) so that tension is consistently applied during the ultrasonic cleaning process. The ratchet (11) has multiple ratchet positions to accommodate different length reamers and/or tension forces. Once the U-bar (16) is secured by the ratchet (11) and water (or another liquid) is poured into the chamber, the transducers (18*a* and 18*b*) may be turned on to clean the reamer. To release tension after the cleaning process was completed, the ratchet (11) is disengaged by pressing down on the U-bar (16) so that the U-bar (16) is released. Then, the reamer may be released from the shaft collars (14*a* and 14*b*) via a variety of step sequences involving the two cables (21*a* and 21*b*) and the cable holders (4*a* and 4*b*).

By applying a lateral tension to a reamer, an entire circumference and length of the flexible body (1B) is stretched and then simultaneously cleaned, as opposed to the conventional method of bending the reamer, which exposes and compresses opposing sides of the reamer. By applying a lateral tension to a reamer, the current invention expedites cleaning as compared to the conventional approach multiple flexing in different directions. By applying a lateral tension to a reamer, the current invention also does not force biodebris further into the flexible body (1B) as occurs with when a side is compressed in the conventional cleaning approach.

The invention claimed is:

1. A device arranged to apply a linear tension to an intramedullary reamer for ultrasonic cleaning, the device comprising:
   a columnar water-tight chamber;
   one or more ultrasonic transducers affixed to an outer surface of the columnar water-tight chamber;
   means for securing the intramedullary reamer within the columnar water-tight chamber; and
   means for applying a linear tension to the secured intramedullary reamer so as to expose an interior portion of the intramedullary reamer for ultrasonic cleaning.

\* \* \* \* \*